(12) United States Patent  
Johansen

(10) Patent No.: US 8,927,271 B1  
(45) Date of Patent: Jan. 6, 2015

(54) COMPOSITIONS AND METHODS FOR DETECTING TARGET ANALYTES

(76) Inventor: Jack T. Johansen, Concord, MA (US)

(*) Notice: Subject to any disclaimer, the term of this patent is extended or adjusted under 35 U.S.C. 154(b) by 562 days.

(21) Appl. No.: 13/011,740

(22) Filed: Jan. 21, 2011

Related U.S. Application Data

(60) Provisional application No. 61/297,159, filed on Jan. 21, 2010.

(51) Int. Cl.
*C12N 5/00* (2006.01)
*C12Q 1/00* (2006.01)

(52) U.S. Cl.
USPC .......................................... 435/325; 435/6.1

(58) Field of Classification Search
None
See application file for complete search history.

(56) References Cited

U.S. PATENT DOCUMENTS

| | | | |
|---|---|---|---|
| 5,225,326 A | | 7/1993 | Bresser et al. |
| 5,539,082 A | * | 7/1996 | Nielsen et al. ................ 530/300 |
| 5,747,349 A | | 5/1998 | van den Engh et al. |
| 5,981,180 A | | 11/1999 | Chandler et al. |
| 6,043,060 A | * | 3/2000 | Imanishi ...................... 435/91.1 |
| 6,110,676 A | | 8/2000 | Coull et al. |
| 6,197,513 B1 | | 3/2001 | Coull et al. |
| 6,268,222 B1 | | 7/2001 | Chandler et al. |
| 6,449,562 B1 | | 9/2002 | Chandler et al. |
| 6,656,687 B1 | | 12/2003 | Hyldig-Nielsen |
| 6,664,045 B1 | | 12/2003 | Hyldig-Nielsen et al. |
| 7,034,133 B2 | * | 4/2006 | Wengel et al. ............... 536/23.1 |
| 7,197,286 B2 | | 3/2007 | Ode et al. |
| 7,267,798 B2 | | 9/2007 | Chandler |
| 7,494,776 B2 | | 2/2009 | Wallace et al. |
| 2001/0055764 A1 | | 12/2001 | Empedocles et al. |
| 2002/0142326 A1 | | 10/2002 | Coull et al. |
| 2005/0009052 A1 | | 1/2005 | Supek et al. |
| 2005/0277197 A1 | | 12/2005 | Chandler et al. |
| 2006/0199196 A1 | | 9/2006 | O'Banion et al. |

FOREIGN PATENT DOCUMENTS

| | | |
|---|---|---|
| WO | WO/01/12862 | 1/2001 |
| WO | WO/01/00876 | 2/2001 |
| WO | WO/03/07817 | 9/2003 |

OTHER PUBLICATIONS

Wentzel et al, J. Bacteriol., 183, 24, 7273-7284 (2001).*
Wallner et al., System. Appl. Microbiol. 19, 569-576 (1996).*
Volna et al., Nuc. Acids, Res. 35(8): 274802758, 2007.*
Heyduk et al., Analy. Biochem., 396:298-303, available Sep. 24, 2009.*
Aman et al., Ann. Rev. Microbiol., 59(1): 143-169, 1995.*
Georgiou et al., Nature Biotechnology, vol. 15:29-34, 1997.*
Product Literature & Product Listing, eBioscience, eFluor Nanocrystals, Website_ebioscience.com, Oct. 2009, 10 pages.
Product Literature, Invitrogen, *Tools for microbiology detection and research*, 2007, 20 pages.
Product Literature, Invitrogen, *Alexa Fluor Dye Selection Guide*, available as of Oct. 2009, 48 pages.
Product Literature, Invitrogen, *Chemical Crosslinking Reagents*, Section 5.2 of Molecular Probes the Handbook, available as of Oct. 2009, 14 pages.
Product Literature, Invitrogen, *Antibody Labeling From A to Z*, available as of Oct. 2009, 12 pages.
Product Literature, Carestream Health, *Kodak X-Sight Nanosphere Secondary Antibody Conjugates & Dye Conjugates*, available as of Oct. 2009, 5 pages.
Bearinger et al., Chemical Tethering of Motile Bacteria to Silicon Surfaces, *Bio Techniques*, 46(3): 209-216 (2009).
Miller, Steve, *Luciferase + Quantum Dot= Self Illuminating Nanocrystal Technologies*, Zymera, Inc. & Zymera 2009 Product List, 3 pages.
Jarvis et al., Practical Platform, *CENEAR*, 87(30): 34-36 (2009).
Jin et al., A Generalized Kinetic Model for Amine Modification of Proteins With Application to Phage Display, *BioTechniques*, 46(3): 175-182 (2009).

* cited by examiner

*Primary Examiner* — Nancy T Vogel
(74) *Attorney, Agent, or Firm* — Brian D. Gildea

(57) ABSTRACT

This invention is directed to compositions and methods for determining target analytes. The compositions disclosed relate to cell-linker-probe complexes. The disclosed methods (including multiplex methods) utilize said cell-linker-probe complexes for target analyte determination.

10 Claims, 5 Drawing Sheets

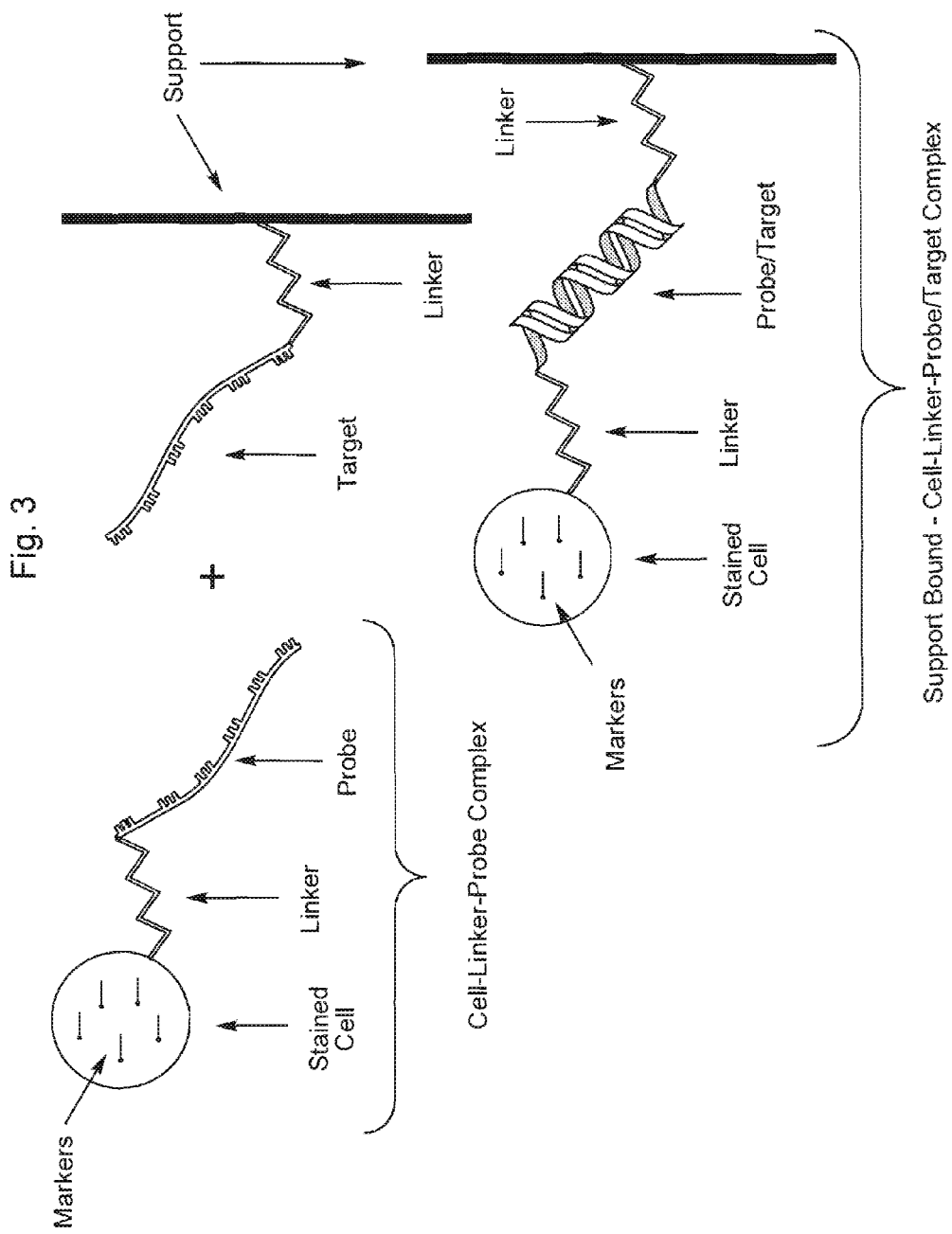

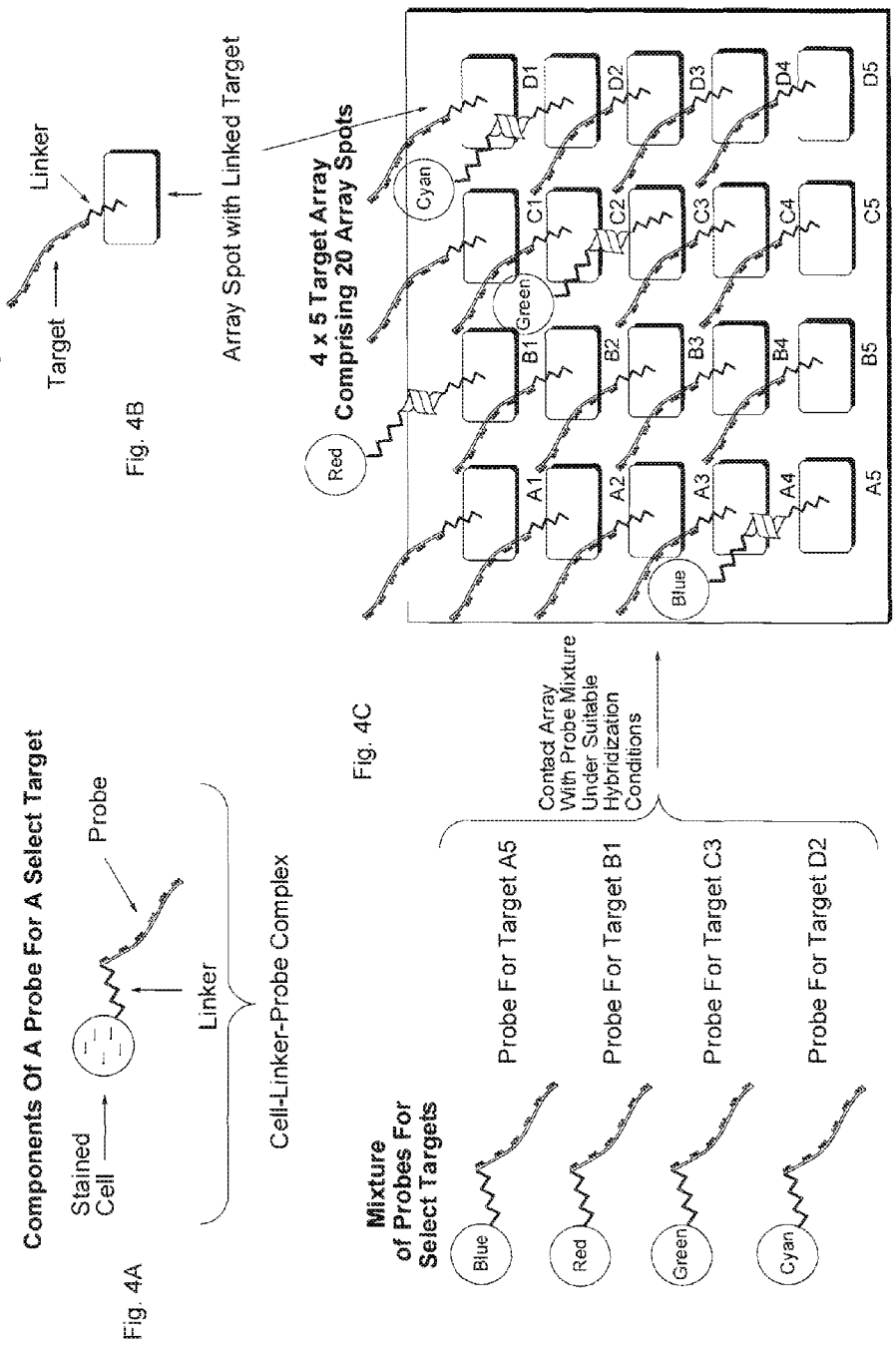

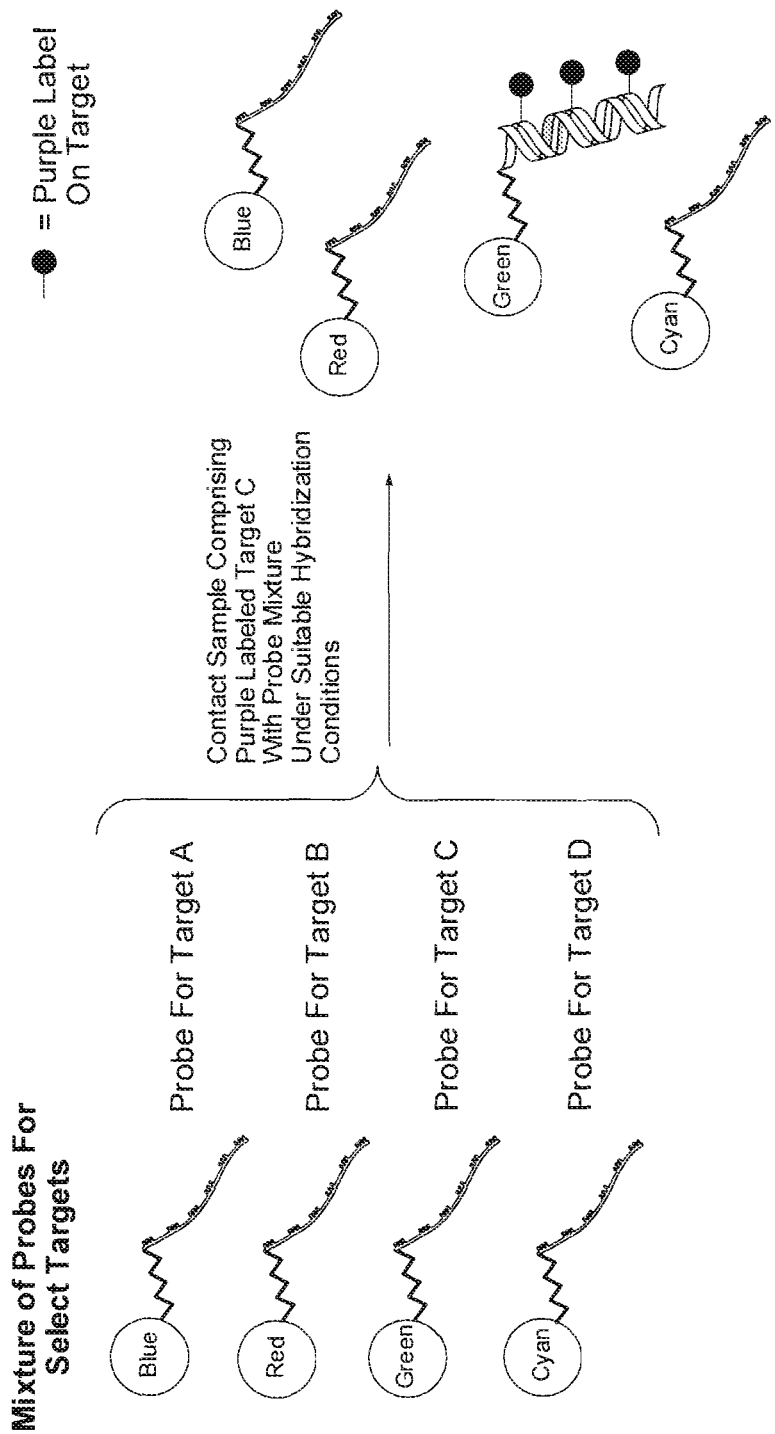

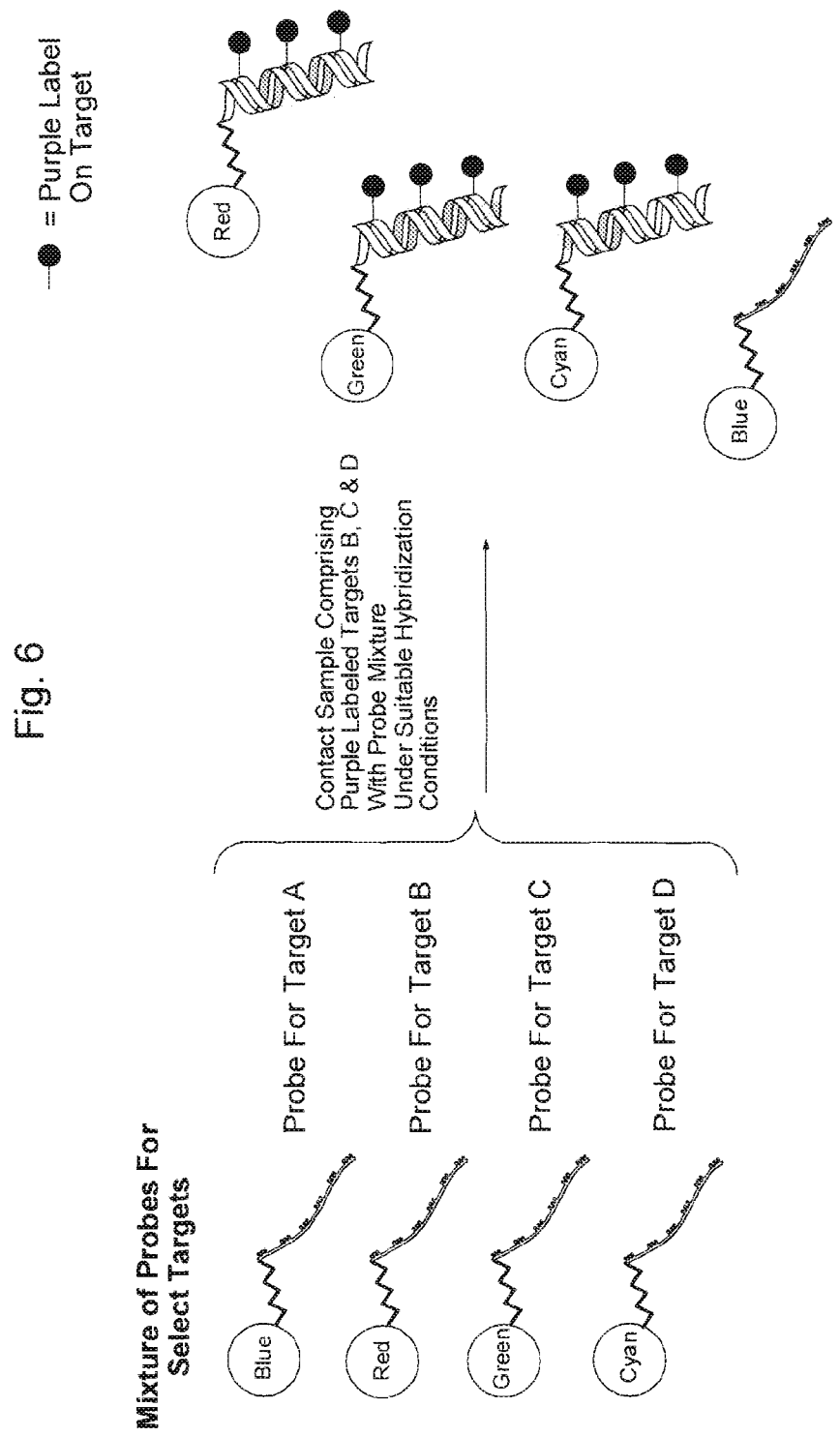

COMPOSITIONS AND METHODS FOR DETECTING TARGET ANALYTES

CROSS REFERENT TO RELATED APPLICATIONS

This application claims the benefit of U.S. Provisional Patent Application Ser. No. 61/297,159, filed on Jan. 21, 2010; herein incorporated by reference for any and all purposes The section headings used herein are for organizational purposes only and should not be construed as limiting the subject matter described in any way.

BRIEF DESCRIPTION OF DRAWINGS

The skilled artisan will understand that the drawings, described below, are for illustration purposes only. The drawings are not intended to limit the scope of the present teaching in any way.

In the drawings, the sizes and relative positions of elements in the drawings are not necessarily drawn to scale. For example, the shapes of various elements and angles may not be drawn to scale, and some of these elements are arbitrarily enlarged and positioned to improve drawing legibility. Further, the particular shapes of the elements as drawn may not be intended to convey any information regarding the actual shape of the particular elements, and may have been selected solely for ease of recognition in the drawings.

FIG. 3 illustrates formation of a support-bound Cell-Linker-Probe/Target Complex formed by hybridization of the probe of a Cell-Linker-Probe Complex to a support-bound Target (wherein the cell is stained with the markers).

FIG. 4A illustrates the components of a stained Cell-Linker-Probe Complex suitable for determining a Select Target (wherein the cell is stained with the markers).

FIG. 4B illustrates the components of an Array Spot comprising a linked Target.

FIG. 4C illustrates a multiplex assay involving hybridization of four differentially stained (e.g. differentially colored) Cell-Linker-Probe Complexes (i.e. probes) to a 4×5 Target Array comprising 20 different Targets (each Target fixed (i.e. linked) to a different spot/location).

FIG. 5 illustrates a solution assay involving hybridization of four differentially stained (e.g. differentially colored) Cell-Linker-Probe Complexes (i.e. probes) to a sample comprising a labeled Target.

FIG. 6 illustrates a solution based multiplex assay involving hybridization of four differentially stained (e.g. differentially colored) Cell-Linker-Probe Complexes (i.e. probes) to a sample comprising labeled Targets.

Figure 1:
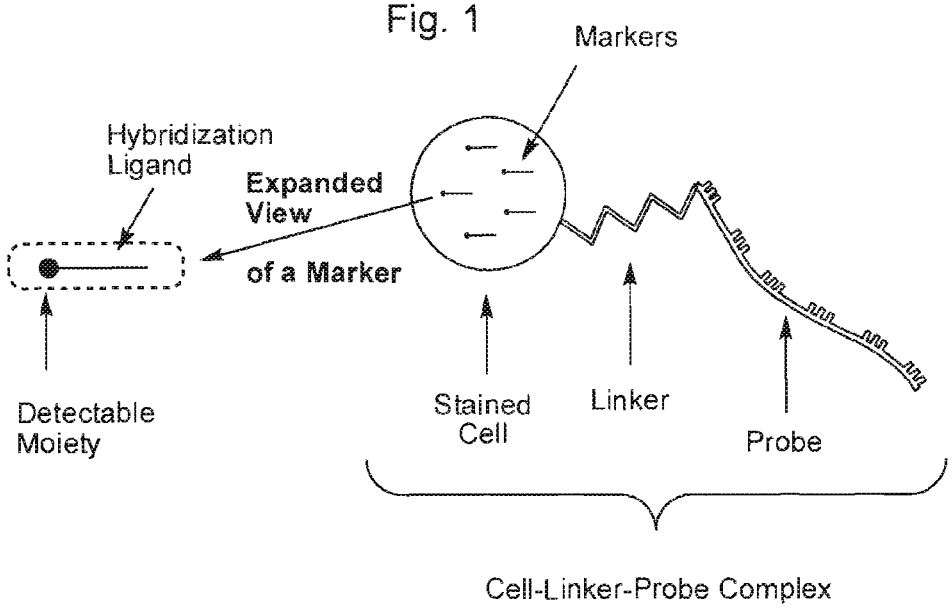
FIG. 1 is an illustration of a Cell-Linker-Probe Complex comprising markers (i.e. the cell is stained with the markers).

All literature and similar materials cited in this application, including but not limited to patents, patent applications, articles, books and treatises, regardless of the format of such literature or similar material, are expressly incorporated by reference herein in their entirety for any and all purposes.

DESCRIPTION

1. Field

This application is directed to the field of target determination using complexes comprising a cell, a linker and a probe.

2. Introduction

The determination of target analytes in biological samples is frequently used, inter alia, in research, in diagnostic and in forensic applications. For example, the target analyte can be a protein, peptide, antibody or nucleic acid (e.g. a gene, messenger ribonucleic acid (mRNA), copy deoxynucleic acid (cDNA), micro ribonucleic acid (miRNA), small interfering ribonucleic acid (siRNA), ribosomal nucleic acid (rRNA) or single nucleotide polymorphism (SNP)). The present invention is directed to new inventive compositions and methods which can be used for target analyte determinations, including use in multiplex assays.

3. Definitions

For the purposes of interpreting this specification, the following definitions will apply and whenever appropriate, terms/phrases used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art will understand that in some specific instances, the embodiment or embodiments can be alternatively described using language "consisting essentially of" and/or "consisting of."

As used herein, "analyte", "target", "target analyte" and "target molecule" are interchangeable and refer to a molecule of interest that may be determined. Non-limiting examples of targets include, but are not limited to, proteins, peptides, nucleic acids (either DNA or RNA), carbohydrates, lipids and steroids. The source of the target analyte, or the sample comprising the target analyte, is not a limitation as it can come from any source. The target analyte or analytes can be natural or synthetic. Non-limiting examples of sources for the target analyte, or the sample comprising the target analyte, include cells or tissues, or cultures (or subcultures) thereof. Other non-limiting examples of target analyte sources include, but are not limited to, crude or processed cell lysates, body fluids, tissue extracts, cell extracts or fractions (or portions) from a separations process such as a chromatographic separation, a 1D electrophoretic separation, a 2D electrophoretic separation or a capillary electrophoretic separation. Body fluids include, but are not limited to, blood, urine, feces, saliva, spinal fluid, mucus, ear wax, puss, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more target analytes that are peptides formed by treatment of the cell lysate with one or more proteolytic enzymes to thereby at least partially digest precursor peptides and/or proteins.

As used herein, "antibody" refers to an immunoglobulin protein, or to a fragment or derivative thereof, which is capable of participating in antibody/antigen binding interaction(s). A discussion of the technical features of antibodies, their fragments, methods for detection of antibodies/antibody fragments and related topics can be found in the Pierce Catalog and Handbook, 1994 (Section T) as well as in Invitrogen Product Literature, *Antibody Labeling From A to Z*, available as least as of October, 2009, 12 pages. Antibodies include, for example, various classes and isotypes of immunoglobulins, such as IgA, IgD, IgE, IgG1, IgG2a, IgG2b, IgG3, and IgM. Antibody fragments include molecules such as Fab, scFv, F(ab')$_2$ and Fab' molecules. Antibody derivatives include antibodies, or fragments thereof, having additions or substitutions, such as chimeric antibodies. Antibodies can be derived from human or animal sources, from hybridomas, through recombinant methods, or in any other way known to the art.

As used herein, "array" or "microarray" refers to a predetermined spatial arrangement of elements (referred to as spots or locations) present on a support or in an arrangement of vessels. Certain array formats can be referred to as a "chip" or "biochip" (M. Schena, Ed. Microarray Biochip Technology, BioTechnique Books, Eaton Publishing, Natick, Mass. (2000)). An array can comprise a low-density number of addressable locations (e.g. 2 to about 12), medium-density (e.g. about a hundred to one thousand addressable locations), or a high-density number (e.g. more than one thousand addressable locations/spots). Typically, the array format can be a geometrically-regular shape (e.g. a square, rectangle or circle) that allows for fabrication, handling, placement, stacking, reagent introduction, detection, and/or storage. The array may be configured in a row and column format, with or without regular spacing between each location. The locations may be bundled, mixed, or homogeneously blended for equalized treatment or sampling. An array may comprise a plurality of addressable locations configured so that each location is spatially addressable for high-throughput handling, robotic delivery, masking, or sampling of reagent(s), or for detection means including scanning by laser illumination and confocal or deflective light gathering.

As used herein, "a plurality of the same or different markers" refers to two or more of the same or different compositions being used as markers. Each composition (e.g. ligand) being used as a marker may comprise one or a plurality of detectable moieties. The compositions may be used individually or as mixtures for purposes of marking the cells. For example, the plurality of markers can be copies of the same labeled hybridization ligand (e.g. with each ligand comprising the same detectable moiety or moieties) bound to different (but identical or substantially identical) rRNA molecules in a cell to thereby, in the aggregate, render the cell detectable. In some embodiments, the plurality of markers can be different hybridization ligands (e.g. with each ligand comprising the same detectable moiety or moieties) wherein said different ligands bind to the same or different rRNA molecules in a cell to thereby, in the aggregate, render the cell detectable. In some embodiments, the plurality of markers may be the same hybridization ligand wherein at least two of the ligands comprise a different detectable moiety and wherein said ligands bind to different (but identical or substantially identical) rRNA molecules in a cell to thereby, in the aggregate, render the cell detectable. In some embodiments, the plurality of markers may be different hybridization ligands wherein each different ligand comprises a different detectable moiety or moieties and wherein said different ligands bind to the same or different rRNA molecules in a cell to thereby, in the aggregate, render the cell detectable.

Figure 2:
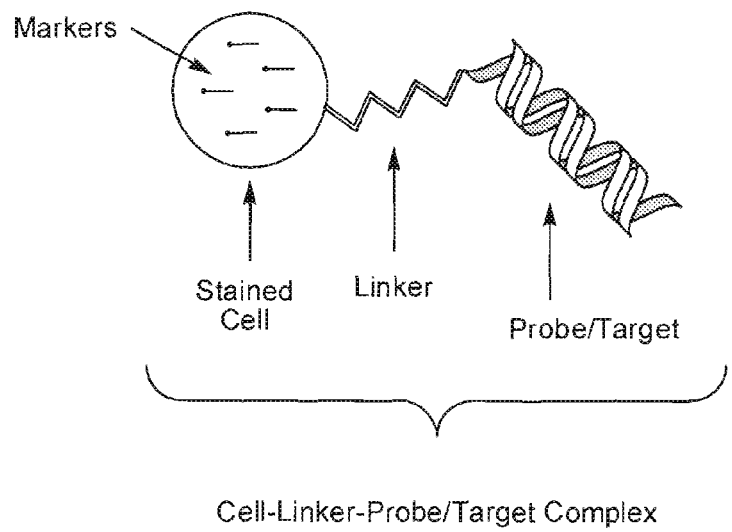
FIG. 2 is an illustration of a Cell-Linker-Probe/Target Complex comprising markers (i.e. the cell is stained with the markers).

As used herein, "capable of binding to a target", "capable of binding to the target" "capable of binding to a target analyte", "capable of binding to the target analyte", "capable of binding to an analyte" or "capable of binding to the analyte" are essentially interchangeable and refer to having the ability to bind to selectively (i.e. specifically bind) bind to the target (target analyte or analyte) under conditions suitable for formation of a probe/target complex wherein the probe is the probe of a cell-linker-probe complex (See for example—FIGS. 2, 3 and 4c).

As used herein, "cell" refers to the basic organizational unit of all living organisms. A cell can be a bacteria, a yeast or can be a single cell of the tissue of a multicellular organism such as an animal, plant or human.

As used herein, "chimera" refers to an oligomer comprising subunits of two or more different classes of subunits. For example, a chimera can comprise subunits of deoxyribonucleic acid (DNA) and locked nucleic acid (LNA), can comprise subunits of DNA and ribonucleic acid (RNA), can comprise subunits of DNA and peptide nucleic acid (PNA), can comprise subunits of DNA, LNA and PNA or can comprise subunits of RNA and LNA, etc. It is to be understood that what the literature refers to as LNA oligomers (or probes) are typically chimeras (according to this definition), since said "LNA oligomers" usually incorporate only one or a few LNA nucleotides. The remaining nucleotides of a LNA oligomer are (as described in various literature references) typically standard DNA or RNA nucleotides.

As used herein, "detectable moiety or moieties" refers to a structural unit (or structural units as the case may be) of a composition (e.g. a hybridization ligand) that renders the composition detectable by instrument and/or method. Non-limiting examples of detectable moieties include fluorophores, chromophores, enzymes, haptens, radioisotopes, quantum dots and radio frequency identification (RFID) tags. In some embodiments, two or more of the foregoing can be used in combination to render the composition detectable or independently (uniquely) detectable.

As used herein, "determining" or "determination" refers to making a decision based on investigation, reasoning and/or calculation. Some examples of determining include detecting, identifying, locating and/or quantifying cells as appropriate based on the usage of the term herein.

As used herein, "in the aggregate" refers to considering relevant subject matter as a whole rather than piecemeal.

As used herein, "labeled hybridization ligands that bind to rRNA" refers to a ligand or ligands that specifically (as compared to non-specifically) hybridize (under suitable hybridization conditions) to rRNA and that comprise one or more detectable moieties wherein said ligands can be used as markers to stain cells. The ligands can be oligomers of nucleic acid (e.g. DNA or RNA). The ligands can be oligomers of nucleic acid analogs (e.g. LNA). The ligands can be oligomers of nucleic acid mimics (e.g. PNA). The ligands can be chimeric oligomers. It is to be understood that a ligand that binds to rRNA is not necessarily inconsistent with the definition of "probe" presented below but that for purposes of this specification, "labeled hybridization ligands that bind to rRNA" has a special definition made with reference to markers used to stain cells.

As used herein, the term "ligand pair" refers to those molecules that bind to one or more other molecules in a specific manner. Because the ligand pair interactions are specific, there is a degree of selectivity that is achieved depending on the nature of the ligands chosen. Non-limiting examples of ligand pair complexes (formed from the component ligands) include antibody/antigen interactions, nucleic acid/nucleic acid interactions (including interactions of nucleic acids with nucleic acid analogs, nucleic acids with nucleic acid mimics, nucleic acids with chimeras as well as interactions between any combination of nucleic acid analogs, nucleic acid mimics and chimeras), enzyme/substrate interactions and receptor/ligand interactions. A non-limiting list of some ligands includes avidin (and its analogs such as streptavidin and Lumavidin™), lectins, carbohydrates, nucleic acids, nucleic acid analogs, nucleic acid mimics, chimeras, antibodies (and antibody fragments) peptides and proteins.

As used herein, "linker" or "cross linker" refers to a single bond or to a composition capable of linking (or that links) a probe to a cell or a target to a support. Examples of linkers and cross linkers are discussed in more detail below.

As used herein, "marker" refers to a composition suitable to mark a cell for determination. A marker comprises a detectable moiety or moieties but it is to be understood from the foregoing however, that a marker may differ from a detectable moiety in that a marker (as used herein) may also refer to a composition of which a detectable moiety is a subcomponent. For example, a marker can be a hybridization ligand comprising one or more detectable moieties wherein said hybridization ligand binds to rRNA of a cell (often referred to in the scientific literature as a ribosomal RNA probe) to thereby stain the cell. A marker can also be a labeled antibody (or antibody fragment) that interacts with, and thereby stains, a cell. In some embodiments, more that one marker (e.g. two hybridization ligands) or marker types (e.g. hybridization ligands and antibodies) can be used to stain a single cell. In some embodiments, a marker is simply a detectable moiety or detectable moieties (without any attached ligand that interacts with the cell) that directly interact with one or more components of the cell to cells to thereby stain the cell or cells (See for example: pages 11-13 of Product Literature, Invitrogen, *Tools for microbiology detection and research,* 2007, 20 pages).

As used herein, "nucleic acid" refers to a nucleobase containing polymer formed from nucleotide subunits composed of a nucleobase, a ribose or 2'-deoxyribose sugar and a phosphate group. Some examples of nucleic acid are DNA and RNA.

As used herein, "nucleic acid analog" refers to a nucleobase containing polymer formed from subunits wherein the subunits comprise a nucleobase and a sugar moiety that is not ribose or 2'-deoxyribose and/or a linkage (between the sugar units) that is not a phosphate group. A non-limiting example of a nucleic acid analog is a locked nucleic acid (LNA: See for example, U.S. Pat. Nos. 6,043,060, 7,053,199, 7,217,805 and 7,427,672). See: Janson and During, "Peptide Nucleic Acids, Morpholinos and Related Antisense Biomolecules", Chapter 7, "Chemistry of Locked Nucleic Acids (LNA)", Springer Science & Business, 2006 for a summary of the chemistry of LNA.

As used herein, "nucleic acid mimic" refers to a nucleobase containing polymer formed from subunits that comprise a nucleobase and a backbone structure that is not a sugar moiety but that can nevertheless sequence specifically bind to a nucleic acid. An example of a nucleic acid mimic is peptide nucleic acid (PNA: See for example, U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, WO92/20702 and WO92/20703). Another example of a nucleic acid mimic is a morpholino oligomer. (See: Janson and During, "Peptide Nucleic Acids, Morpholinos and Related Antisense Biomolecules", Chapter 6, "Morpholinos and PNAs Compared", Springer Science & Business, 2006 for a discussion of the differences between PNAs and morpholinos).

As used herein, "nucleobase" refers to those naturally occurring and those non-naturally occurring heterocyclic moieties commonly known to those who generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

As used herein, "operably links" refers to linking a composition to another in such a way that one or both compositions remain operable. For example, with respect to linking a probe to a cell via a linker, the probe remains capable of binding to its respective target and the cell remains detectable or independently detectable (or capable of being made detectable or independently detectable). In this way, the linker operably links the cell to the probe.

As used herein, the term "peptide nucleic acid" or "PNA" refers to any oligomer (that is not a chimera) comprising two or more PNA subunits (residues), including any of the polymers referred to or claimed as peptide nucleic acids in U.S. Pat. Nos. 5,539,082, 5,527,675, 5,623,049, 5,714,331, 5,718, 262, 5,736,336, 5,773,571, 5,766,855, 5,786,461, 5,837,459, 5,891,625, 5,972,610, 5,986,053 and 6,107,470. In preferred embodiments, a PNA is an oligomer (that is not a chimera) comprising two or more subunits of the formula:

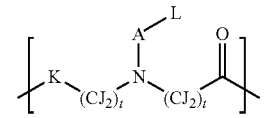

wherein, each J is the same or different and is selected from the group consisting of H, $R^1$, $OR^1$, $SR^1$, $NHR^1$, $N(R^1)_2$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; —$(CJ_2)_s$- and a group of the formula; —$(CJ_2)_sC(O)$—, wherein, J is defined above and each s is 1, 2, 3, 4 or 5. Each t is 1 or 2 and each u is 1 or 2. Each L is the same or different and is independently selected from adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties. In some embodiments, a PNA subunit consists of a naturally occurring or non-naturally occurring nucleobase attached to the aza nitrogen of the N-[2-(aminoethyl)]glycine backbone through a methylene carbonyl linkage.

As used herein, "probe" refers to a composition used to obtain specific information for research, diagnostics and/or forensic purposes. A probe can be one member of a ligand pair, wherein the other member of the ligand pair is the target (a.k.a. analyte, target analyte or target molecule) as discussed herein such that, for example, the probe is selected for determining the presence, absence, location and/or quantity of the target in a sample. Non-limiting examples of probes include nucleic acid oligomers, nucleic acid analog oligomers, nucleic acid mimic oligomers, chimeras, antibodies and haptens. A probe may comprise a natural or synthetically introduced functional group for attachment to a linker or to a surface.

As used herein, "quantum dot" refers to an inorganic crystallite between about 1 nm and about 1000 nm in diameter or any integer or fraction of an integer there between, generally between about 2 nm and about 50 nm or any integer or fraction of an integer there between, more typically about 2 nm to about 20 nm (such as 2, 3, 4, 5, 6, 7, 8, 9, 10, 11, 12, 13, 14, 15, 16, 17, 18, 19, or 20 nm). A semiconductor nanocrystal is capable of emitting electromagnetic radiation upon excitation (i.e., the semiconductor nanocrystal is luminescent) and includes a "core" of one or more first semiconductor materials, and may be surrounded by a "shell" of a second semiconductor material. A semiconductor nanocrystals core surrounded by a semiconductor shell is referred to as a "core/shell" semiconductor nanocrystal. The Surrounding "shell" material typically has a bandgap energy that is larger than the bandgap energy of the core material and can be chosen to have an atomic spacing close to that of the "core" substrate. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof. In the scientific and patent literature the terms "semiconductor nanocrystal," "quantum dot", "Qdot™ nanocrystal" or simply "nanocrystal" are used interchangeably. For purposes of this specification, these terms are also equivalents of "quantum dot" as defined above. Some examples of commercially available quantum dots can be found in: Miller, Steve, Luciferase+ Quantum Dot=Self Illuminating Nanocrystal Technologies, Zymera, Inc & Zymera 2009 Product List.

As used herein, "select target" refers to a target that is selected based on its known relation to a condition of interest that can be determined by practice of an assay. For example, a target can be selected to determine the presence, location and/or quantity of a pathogen such as *E. coli* in a sample. In a multiplex assay for example, one select target can be selected for a pathogen such as *E. coli* and a second select target can be selected for a second pathogen such a *listeria*. Numerous targets (three, four, five, six, seven, eight, nine, ten or more) can be determined in a single assay where the marked cells of different cell-linker-probe complexes are differentially labeled.

As used herein, "stained" means that a cell is directly or indirectly marked for detection with detectable moieties (i.e. render the cell identifiable). For example, the cell can be stained with fluorescent markers (or independently detectable fluorescent markers) such that the cell or cells are detectable using a fluorescent microscope as described in U.S. Pat. No. 6,664,045 (See in particular FIGS. 3I-3IV (of U.S. Pat. No. 6,664,045) and the discussion associated therewith in Example 10 at col. 24-25).

As used herein, "surface of a cell" or "surface of the cell" refers to the outermost surface of the cell or the membrane (including components that are part of, or included within, said membrane) covering a cell (which membrane may extend a small distance into the cell), as appropriate.

As used herein, "support", "solid support" and "solid carrier" are interchangeable and refer to any solid phase material upon which a target is synthesized, attached, ligated, labeled, manipulated or otherwise immobilized. Support encompasses terms such as "resin", "solid phase" and "surface". A support may be composed of organic polymers such as plastic (e.g. polystyrene, polyethylene, polypropylene, polyfluoroethylene, polyethyleneoxy, and polyacrylamide, as well as co-polymers and grafts thereof). A support may also be inorganic, such as glass, silica, controlled-pore-glass (CPG), reverse-phase silica, silver or gold. The configuration of a support may be in the form of beads, microscope slides, microtitre plates, membranes, arrays, spheres, particles, granules, a gel, or a surface. Surfaces may be planar, substantially planar, or non-planar. Supports may be porous or non-porous, and may have swelling or non-swelling characteristics. A support may be configured in the form of a well, depression or other container, vessel feature or location. A plurality of supports may be configured in an array at various locations, addressable for robotic delivery of reagents, or by detection means including scanning by laser illumination and confocal or deflective light gathering.

As used herein, "support-bound" means immobilized on, or to, a support.

As used herein, "tissue" refers to an aggregate of cells, usually of a particular kind, together with their intercellular substance that form one of the structural materials of a plant, an animal or a human.

As used herein, "under conditions suitable for the probe to bind to the target" refers to conditions under which the probe binds to the target in a selective (i.e. specific) or substantially selective manner such that non-specific binding of probe to non-target moieties is minimized or eliminated.

As used herein, "uniquely identifiable" refers to conditions under which two or more cells with distinguishable properties can be distinguished. For example, one cell may comprise red fluorescent markers and another cell may comprise green fluorescent markers. Accordingly, said two cells are uniquely identifiable using a properly equipped microscope (See for example: U.S. Pat. No. 6,656,687 at FIG. 6 and the associated discussion at Example 12) since the green cells can be distinguished from the red cells.

4. General

It is to be understood that the discussion set forth below in this "General" section can pertain to some, or to all, of the various embodiments of the invention described herein.

Synthesis, Modification and Labeling of Nucleic Acids and Nucleic Acid Analogs

Nucleic acid oligomer (oligonucleotide and oligoribonucleotide) synthesis has become routine. For a detailed description of nucleic acid synthesis please see Gait, M. J., "Oligonucleotide Synthesis: a Practical Approach" IRL Press, Oxford England. Persons of ordinary skill in the art will recognize that labeled and unlabeled oligonucleotides (DNA, RNA and synthetic analogues thereof) are readily available.

They can be synthesized using commercially available instrumentation and reagents or they can be purchased from commercial vendors of custom manufactured oligonucleotides.

PNA Synthesis and Labeling

Methods for the chemical assembly of PNAs are well-known (See: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470; all of which are herein incorporated by reference for their information pertaining to peptide nucleic acid synthesis, modification and labeling. Chemicals and instrumentation for the support-bound automated chemical assembly of peptide nucleic acids are commercially available. Both labeled and unlabeled PNA oligomers are likewise available from commercial vendors of custom PNA oligomers (See the worldwide web at: 1) panagene.com/pna-oligomers.php, 2) biosyn.com/pna_custom.aspx or 3) crbdiscovery.com/pna/). Additional information on PNA synthesis and labeling can be found in Peter E. Nielsen, "Peptide Nucleic Acids", Taylor and Francis, 2004.

Because a PNA is a polyamide, it has a C-terminus (carboxyl terminus) and an N-terminus (amino terminus). For the purposes of the design of a hybridization ligand (e.g. probe) suitable for antiparallel binding to a target (the preferred orientation), the N-terminus of the PNA oligomer is the equivalent of the 5'-hydroxyl terminus of an equivalent DNA or RNA oligonucleotide.

Some non-limiting methods for labeling PNAs are described in U.S. Pat. No. 6,110,676, WO99/22018, WO99/21881, WO99/49293 and WO99/37670 or are otherwise well known in the art of PNA synthesis.

Chimera Synthesis and Labeling/Modification

Chimeras are oligomers comprising subunits of different monomer types. In general, it is possible to use labeling techniques (with or without adaptation) applicable to the monomer types used to construct the chimera. For example, labeling techniques used to label nucleic acids can usually be directly applied to LNA chimeras and other nucleic acid analogs. For nucleic acid mimics, such as PNA, peptide labeling techniques are often employed.

Indeed, various labeled and unlabeled chimeric molecules are reported in the scientific literature or available from commercial sources (See: U.S. Pat. No. 6,316,230 and WO2001/027326 and See the worldwide web at: biosyn.com/PNA_Synthesis.aspx, and sigmaaldrich.com/life-science/custom-oligos/dna-probes/product-lines/lna-probes.html). Therefore it is clear that persons of skill in the art can either prepare them or purchase them from readily available sources.

Antibody Preparation and Labeling

Antibodies that bind to specific antigens can be produced by various methods (See for example: Jarvis et al., *Practical Platform, CENEAR*, 87(30): 34-36 (2009)). Once raised to their antigen and isolated, the isolated antibodies (which are proteins) can be labeled and/or linked to other compositions such as a cell or a surface (See: Product Literature, *Invitrogen, Antibody Labeling From A to Z*, available as least as of October, 2009, 12 pages; Jin et al., *A Generalized Kinetic Model For Amine Modification Of Proteins With Application To Phage Display, BioTechniques,* 46(3): 175-182 (2009)) and Miller, Steve, *Luciferase+Quantum Dot=Self Illuminating Nanocrystal Technologies*, Zymera, Inc. & Zymera 2009 Product List, 3 pages).

Labels

Non-limiting examples of detectable moieties (labels) suitable for directly labeling hybridization ligands, antibodies or antibody fragments or other compositions (e.g. to thereby generate a marker) used in the practice of this invention include a dextran conjugate, a branched nucleic acid detection system, a chromophore, a fluorophore, a spin label, a radioisotope, an enzyme, a hapten, a chemiluminescent compound, a quantum dot or a RFID tag, or any combination of two or more of the foregoing.

Some examples of haptens include 5(6)-carboxyfluorescein, 2,4-dinitrophenyl, digoxigenin, and biotin.

Some examples of fluorochromes (fluorophores) include 5(6)-carboxyfluorescein (Flu), 6-((7-amino-4-methylcoumarin-3-acetyl)amino)hexanoic acid (Cou), 5 (and 6)-carboxy-X-rhodamine (ROX), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from GE Healthcare, Life Sciences, Piscataway, N.J.), JOE, TAMRA or the Alexa dye series (Invitrogen, Carlsbad, Calif.—See for example: Product Literature, Invitrogen, *Alexa Fluor Dye Selection Guide*, available at least as of October, 2009, 48 pages).

Some examples of enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and soy bean peroxidase (SBP).

Some examples of radioisotopes include $^{14}$C, $^{32}$P, $^{129}$I and $^{99}$Tc.

In some embodiments, spin labels can be used to mark cells for determination. Spin labels are organic molecules which possess an unpaired electron spin, usually on a nitrogen atom. For example, oligomers can be labeled with a spin label as described in U.S. Pat. No. 7,494,776. Said labeled oligomer can then, for example, be used as a marker to mark cells for determination.

In some embodiments, RFID tags can be used to mark cells for determination as described in published US Patent Application No: 2006/0199196 (See: paragraphs 79-94). Thus, in some embodiments, RFID tags themselves, or RFID tags linked to oligonucleotides (i.e. RFID tags linked to a ligand or ligands that bind to rRNA), can be used as markers.

According to U.S. Pat. No. 7,498,177, a translocation peptide can be used in combination with quantum dots to thereby allow the quantum dots to penetrate into the nucleus of cells. Thus, in some embodiments, quantum dots can be used to mark cells for determination, whether or not linked to a ligand. Various types of quantum dots are known in the art. For example see: Miller, Steve, *Luciferase+Quantum Dot=Self Illuminating Nanocrystal Technologies*, Zymera, Inc. & Zymera 2009 Product List; and Product Literature & Product Listing, eBioscience, eFluor Nanocrystals, website_ 2009, 10 pages.

Detectable and Independently Detectable Moieties/Multiplex Analysis

In some embodiments of this invention, a multiplex assay is performed. In a multiplex assay, numerous conditions of interest are simultaneously or sequentially examined. Multiplex analysis relies on the ability to sort sample components, or the data associated therewith, during or after the assay is completed. In a multiplex assay, one or more distinct independently detectable moieties (or a unique combination of moieties) can be used to uniquely mark (i.e. stain) two or more different cells wherein each uniquely marked cell (or cell type) comprises a unique linked probe that is directed to a unique target of interest (i.e. a unique "select target"). The ability to differentiate between and/or quantify each of the uniquely marked cells provides the means to multiplex the assay because the data that correlates with each uniquely marked (i.e. stained) cell can be correlated with the presence, absence, location and/or quantity of the unique target sought to be determined (See for example, FIGS. 4 and 6). Consequently, the multiplex assays of this invention may be used to simultaneously or sequentially determine the presence, absence, location and/or quantity of two or more targets in the same sample and in the same assay.

Specificity:

As noted above, probe/target complexes are formed under conditions that permit specificity of binding. Specificity of hybridization (i.e. the sequence specific binding of a hybridization probe to a nucleic acid target) is a function of various factors related to stringency and/or blocking strategy(ies). Specificity of binding also applies to antibody binding or the binding of members of any other type of ligand-ligand pair. Like hybridization specificity, specificity of binding of antibodies to antigens (or binding of one member of a ligand pair to another member) is also condition dependent. In principle, conditions are selected to optimize specificity so that non-specific binding is minimized or eliminated. Nevertheless, it is to be understood that specificity of binding is a relative term which also depends on many factors, including the nature (e.g. affinity) of the compositions forming the binding complex. Below is a non-limiting discussion of various conditions/considerations. Using no more than routine experimentation in combination with the disclosure provided herein, persons of skill in the art will be able to achieve suitable conditions so that binding (or hybridization) of particular probes to their respective targets is specific (such practice of the method produces an accurate and reproducible result). In some embodiments, this can be accomplished using commercially available buffers.

Blocking Probes:

In hybridization reactions, blocking probes (made of nucleic acids, nucleic analogs, nucleic acid mimics and/or chimeras) can be used to suppress the binding of probes to a non-target and thereby improve specificity of the formation of probe/target complexes. Especially effective blocking probes are PNA oligomers (See: Coull et al., U.S. Pat. No. 6,110,676, herein incorporated by reference and Fiandaca et al. "PNA Blocker Probes Enhance Specificity In Probe Assays", Peptide Nucleic Acids: Protocols and Applications, pp. 129-141, Horizon Scientific Press, Wymondham, UK, 1999)).

Hybridization Conditions/Stringency:

Persons of ordinary skill in the art will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Blocking probes (See the section immediately above for a discussion of blocking probes) may also be used as a means to improve discrimination beyond the limits possible by mere optimization of stringency factors. Optimal stringency for forming a probe/target complex is often found by the well-known technique of fixing several of the aforementioned stringency factors and then determining the effect of varying a single stringency factor. The same stringency factors can be modulated to thereby control the stringency of hybridization of a nucleic acid mimic, nucleic acid analog or chimera to a nucleic acid target (e.g. a sequence within rRNA, mRNA or chromosomal DNA), except that for some of these modified oligomers (e.g. PNA) the hybridization may be fairly independent of ionic strength. Optimal or suitable stringency for an assay may be experimentally determined by examination of each stringency factor until the desired degree of discrimination is achieved. Nevertheless, optimal stringency is not required. Rather, all that is required is that the non-specific binding of probes to their respective targets is minimized in the assay to the extent necessary to achieve an accurate and reproducible result. We refer to this as "suitable hybridization conditions". As noted, various hybridization buffers (for hybridization events) and binding buffers (for binding events) are commercially available. Such buffers, in combination with temperature control, often produce suitable hybridization conditions or suitable binding conditions, as appropriate.

Suitable Antibody Binding Conditions

Suitable antibody binding conditions comprise conditions suitable for binding an antibody to its antigen. Factors effecting antibody binding to its antigen (or for the binding of the ligands of a ligand-ligand complex) are substantially similar to those described above for hybridization and can be optimized in a similar manner. Suitable antibody binding conditions for various antibodies are known to persons of skill in the art. For those that are not, they can be determined. Suitable antibody binding buffers are also commercially available.

Therefore; using the disclosure provided herein; with or without additional routine experimentation, persons of skill in the art can determine suitable antibody binding conditions. By way of additional general guidance to the practitioner, methods for preparing and using antibodies can be found in numerous references including: Molecular Probes Of The Nervous System, Volume 1, "Selected Methods For Antibody and Nucleic Acid Probes", Cold Spring Harbor Laboratory Press, 1993 by S. Hockfield et al.

Harmonization of Suitable Hybridization Conditions & Suitable Antibody Binding Conditions and Other Assay Requirements When practicing the methods disclosed herein, persons of skill in the art may find it useful to harmonize the hybridization conditions, antibody binding conditions and other assay conditions (or conditions for ligand-ligand binding). For example, in some embodiments, the staining of cells with one or more hybridization probes may be performed simultaneously with, prior to, or subsequent to, an antibody binding event. Because adjustment of the same variables (pH, salt concentration etc.) is commonly involved, aided by no more than routine experimentation, those of skill in the art will easily be able to harmonize conditions so that the assay produces a satisfactory result. A discussion of some of the problems and related solutions for harmonizing conditions for using antibody probes and hybridization probes in a single assay can be found in Goldbard et al. (U.S. Pat. No. 6,524, 798) and Aβmus et al., "*Improved In Situ Tracking of Rhizosphere Bacteria Using Dual Staining with Fluorescence-Labeled Antibodies and rRNA-Targeted Oligonucleotides*", *Microb. Ecol.*, 33: 32-40 (1997). It is also worth noting that the use of nucleic acid mimics, such as PNA, can often simplify the harmonization process because some of these probe types bind to complementary nucleic acid (as compared with nucleic acid/nucleic acid interactions) under a wide range of conditions, thereby permitting one to tailor the conditions more closely to those suitable for the antibody-antigen and/or other ligand-ligand binding.

Cells

With respect to cells used to form cell-linker-probe complexes, any single cell that can be marked for detection can be used. Thus, the cell can be a bacteria or yeast. The cell can be a single cell of the tissue of a multicellular organism such as an animal, plant or human. However, it is to be understood that some cell types will prove more useful than others. For example, cells that are robust or than can be easily manipulated within the context of a particular assay may prove to be more useful. Persons of ordinary skill in the art, exercising no more than routine experimentation and the discussion provided herein, will be able to test and determine which cell types are better suited for particular assays.

Cells can be easily marked for determination using various methods. The markers can mark any part of the cell. The markers can mark the surface of the cell (so long as it remains possible to link the probe to the cell), the cytoplasm of the cell (or components thereof) or the nucleus of the cell. The markers can mark two or more of the foregoing. It is to be understood that how the cell is marked is not a limitation.

For example, cells can be marked using in-situ hybridization (See: U.S. Pat. No. 5,225,326 and published US patent application No. 2002/0142326). Both, universal or specific marker ligands (referred to as probes in the cited references but referred to herein as "labeled hybridization ligands that bind to rRNA") can be used to mark various types of bacteria and/or yeast (See for example: U.S. Pat. No. 6,280,946, U.S. Pat. No. 6,664,045 and WO03/073817). The ligands can be modified with any suitable detectable moiety or moieties (label or labels), several of which are discussed above. Uniquely marked cells can be determined simultaneously using a microscope or slide scanner (See for example: U.S. Pat. No. 6,656,687, U.S. Pat. No. 6,664,045 and WIPO application No. 03/073817) or sequentially using a flow cytometer (See for example: U.S. Pat. Nos. 5,981,180, 7,267,798 and WIPO application No. 03/073817). Various other methods for marking cells (including differentially marked cells) are known in the art (See for example: published WIPO application No. 03/073817).

It is an advantage that the cells can be marked at any time. The cells can be marked (with the markers) before the assay is performed. The cells can be marked during the assay. The cells can be marked at any time prior to determining cell-linker-probe/target complexes. Thus, in some embodiments, it may be preferable to sell cell-linker-probe complexes wherein the cell(s) is/are unmarked. In some embodiments, it may be preferable to sell cell-linker-probe complexes where in the cell(s) is/are marked (i.e. stained).

In some embodiments, it may be preferable to sell one or more of the parts of a cell-linker-probe complex with or without additional reagents/instructions. For example, in some embodiments, it may be preferable to sell (for example a kit comprising) two or more of the components of the cell-linker-probe complex. For example, it may be preferable to sell (for example a kit comprising) probes and linkers (and optionally a marker) wherein a customer selects his/her own cell(s) such that the customer can prepare the cell-linker-probe complex. Alternatively, it may preferable to sell the cells (marked or unmarked) comprising a linker activated for attachment to a probe of the customer's selection. All other possible combinations of probe(s), linker(s), cell(s) and marker(s) are expressly contemplated herein.

Cell Functional Groups/Surface

It is to be understood that the cell of a cell-linker-probe complex is linked to the probe by a linker. Typically, the linking occurs by reaction of a functional group on the surface of the cell with a functional group of the linker or probe. Cells comprise numerous surface functional groups. For example, the hydroxyl, phenol, thiol, carboxy and amine groups of various amino acids of surface proteins are often accessible for this purpose. Similarly, the functional groups of various surface carbohydrates are also accessible for this purpose. These groups can also be used to introduce other functional groups onto the surface of the cell to thereby more easily link the probe to the cell. A listing of various nucleophilic and electrophilic functional groups that can be used can be found in the TABLE set forth below (under the heading: "Functional Groups").

It is also to be understood that the phrase "surface of the cell" is intended to encompass more than just the outermost region of the cell. A cell surface is dynamic in composition and structure. For example, a surface protein to which a linker attaches (while functional groups of the protein is on its outermost surface) may reorient within the cell membrane such that the functional group to which the linker attached is now below the outermost surface, yet the probe remains operably linked to the cell. Therefore, "surface of the cell" is intended to encompass any molecule or structure associated with the cell's surface to which a linker or probe can be attached such that the probe remains "operably linked" to the cell even if said attachment is somewhat below the outermost region of the cell (Also see the definition of "surface of a cell" at page 10, above).

Cell Morphology

It is an advantage of the present invention that certain types of cells possess a unique morphology. In addition to the markers, morphology of the cells can be used to either confirm the identity of a cell else introduce a second level of differentiation, for example, in a multiplex assay.

For example, bacilli tend to be rod-like whereas streptococci tend to be spherical (See the worldwide web at: en.wikipedia.org/wiki/Bacterial_cell_structure#Cell_morphology and en.wikipedia.org/wiki/File:Bacterial_morphology_diagram.svg) In some assays, it may be that determining a yellow stained rod-like cell will confirm the presence, absence, location and/or quantity of a sought after target. In this case, the shape of the cell may be used to distinguish signal from noise in the assay.

Is some (multiplex) assays, multiple cell types may be used wherein at least two cell types of different morphology are stained with, for example, a yellow marker. In this case, the presence, absence, location and/or quantity of a particular target can be determined based, for example, on whether or not the yellow marked (i.e. stained) cell (of the cell-linker-probe/target complex) is identified as a rod or sphere. Of course an assay using this methodology can be further developed (further multiplexed) using cells of other known morphologies.

Probes

Any probe that can be used to determine a select target and that can be operably linked to a cell is contemplated by this invention. The probe can be an oligomer (i.e. a nucleic acid, a nucleic acid analog, a nucleic acid mimic or a chimera). The probe can be an antibody or antibody fragment. The probe can be an aptamer. The probe can be a peptide or protein.

The probes specified herein are linked to the cell through a linker. Typically, the probe is linked to the linker by reaction of a functional group of the probe with a functional group of the linker. Thus, the probes disclosed herein will comprise a functional group. Said functional group can be native to the probe or be added by synthetic modification of the probe. A listing of various nucleophilic and electrophilic functional groups that can be used can be found in the TABLE set forth below. Persons of ordinary skill in the art will be able to determine whether or not a probe requires modification. The nature and properties of the linker are discussed below.

It is to be understood that numerous probes exist in the biological arts and that the nature of a probe (for purposes of this invention) is not intended to be limited except as specifically disclosed herein.

Linkers

Linkers can be used to link the probe to the cell. Linkers can also be used to link targets to surfaces. As used herein, the linker can be a covalent bond. If the linker is a covalent bond, a functional group of the probe reacts directly with a functional group of the surface of the cell.

However, the linker is more typically a carbon containing moiety comprising two (or more) functional groups, one functional group for linking the probe to the linker and one functional group for linking the cell to the linker. The two (or more) functional groups can be the same or they can be different. For example, the two functional groups of the linker can be the same; i.e. homobifunctional (e.g. both N-hydroxysuccinimidyl esters) or different; i.e. heterobifunctional (e.g. one functional group can be a N-hydroxysuccinimidyl ester and the other can be an isothiocyanate). Numerous alternative functional groups can be found in the TABLE, below.

In some embodiments, the linker can comprise from 1 to 20 carbon atoms. For example, a linker may comprise one or more aminoalkyl carboxylic acids (e.g. aminocaproic acid), the side chain of an amino acid (e.g. the side chain of lysine or ornithine), other natural amino acids (e.g. glycine, alanine, leucine, etc.), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane).

In some embodiments, a linker may have the formula: $-Y-(O_m-(CW_2)_n)_o-Z-$ wherein each end of the formula represents the attachment point to each of the probe and cell (in either orientation) and wherein the chemical linkages are omitted. The group Y can be a single bond. The group Y can be have the formula: $-(CW_2)_p-$, $-C(O)(CW_2)_p-$, $-C(S)(CW_2)_p-$ or $-S(O_2)(CW_2)_p$. The group Z can have the formula Y (defined above), NH, $NR^2$, S or O. Each W is independently H, $R^2$, $-OR^2$, F, Cl, Br or I; wherein, each $R^2$ is independently selected from the group consisting of: $-CX_3$, $-CX_2CX_3$, $-CX_2CX_2CX_3$, $-CX_2CX(CX_3)_2$, and $-C(CX_3)_3$. Each X is independently H, F, Cl, Br or I. Each m is independently 0 or 1. Each n, o and p is independently a integer from 0 to 10.

There are numerous commercially available linkers/cross linkers that can be used to link the cell to the probe. As noted, linkers can be homobifunctional or heterobifunctional. Various examples of suitable commercial cross-linkers that can be used to link the probes to the cells are available from Pierce Chemical Company (See: Pierce Catalog and Handbook, 1994, Section O, under the heading: "Cross-linking/Protein Modification). Some other suitable linkers are described in U.S. Pat. No. 6,197,513. The linkers disclosed in U.S. Pat. No. 6,197,513 can be used to modify the probes wherein the aryl amine functional group of each linker used to link the linker (and hence also the probe) to a surface protein (or other membrane component) of the cell. Still other suitable cross linkers are described in Invitrogen, Product Literature, *Chemical Crosslinking Reagents*, Section 5.2 of Molecular Probes The Handbook, available at least as of October, 2009, 14 pages.

Moreover, the use of cross linkers to tether (i.e. link) living bacteria to silicon surfaces is described in Bearinger et al., *Chemical Tethering Of Motile bacteria to Silicon Surfaces*, BioTechniques, 46(3): 209-216 (2009). These authors demonstrated that either amine groups of the cell surface or carboxy groups of the cell surface could be reacted with respective functional groups of the cross linkers to thereby immobilize the bacteria to the surfaces. According to applicant's invention, the cross linkers would be used to tether (i.e. link) a cell or cells (through functional groups present on the surface of the cell) to a probe or probes. The fact that the chemical tethering of bacteria to the silicon surfaces could be accomplished with various bacteria without killing the bacteria demonstrates that the conditions for linking the bacteria to surfaces or other structures, such as probes, is mild and not likely to render a probe non-operable for hybridization or binding under suitable hybridization conditions or suitable binding conditions (as appropriate).

All of the foregoing examples are for illustration purpose and not intended to be limiting in any way.

Functional Groups

As noted above, in some embodiments a functional group of a cell reacts with a functional group of the linker (See for example: Bearinger et al., *Chemical Tethering Of Motile bacteria to Silicon Surfaces*, BioTechniques, 46(3): 209-216 (2009) wherein the functional group of the cell can be either an amine or a carboxyl group). Similarly, a functional group of the probe reacts with a functional group of the linker (See for example: U.S. Pat. No. 6,110,676, WO99/22018, WO99/21881, WO99/49293 and WO99/37670). The result of these reactions is the cell-linker-probe complex. In practice, these reactions proceed essentially as described in for example: Product Literature, Invitrogen, *Chemical Crosslinking Reagents*, Section 5.2 of Molecular Probes The Handbook, available at least as of October, 2009, 14 pages, at for example FIG. 5.1 or 5.6, wherein $R^1$ and $R^2$ are the cell and the probe, or vice versa. As noted previously, numerous cross linkers are available and these illustrations are not intended to be limiting in any way. Similarly, cross linking reactions can be performed essentially as described in: Bearinger et al., *Chemical Tethering Of Motile bacteria to Silicon Surfaces*, BioTechniques, 46(3): 209-216 (2009), wherein the cell-linker moiety is linked to a probe rather than to a silicon surface. The reactions are described in more general terms as follows.

It is well accepted that one of the two functional groups of each the cell/linker reaction and each linker/probe reaction is an electrophile and the other is a nucleophile. The table below lists various possible electrophilic and nucleophilic groups and the resulting chemical linkage. The covalent (chemical) linkage can be used to link a cell or probe to the linker using either orientation. Persons of skill in the art will recognize that properly functionalized cells, probes and linkers can be used to thereby form the cell-linker-probe complex.

TABLE

| Electrophilic Group | Nucleophilic Group | Resulting Covalent Linkage |
|---|---|---|
| activated esters | amines/anilines | carboxamides |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| akyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |

TABLE-continued

| Electrophilic Group | Nucleophilic Group | Resulting Covalent Linkage |
|---|---|---|
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/aniline | sulfonamides |
| sulfonyl halides | phenols/alcohols | sulfonate esters |

Operably Linking Probes to Cells

The probes are operably linked to the surface of the cells. By operably linked we mean that the probes, when linked to the cells, remain able to specifically bind to their respective targets and thereby form cell-linker-probe/target complexes under suitable hybridization/binding conditions.

Generally speaking, linkers that enable the probe to distance itself from the cell are likely to be more suitable than embodiments where the probe is held in close relation to the cell. Simply stated, probes which are at a distance from the cell should be more easily able to interact with the target. Moreover, the phobicity or hydrophobicity of the linker may also vary and affect results. Preferred choices for the phobicity or hydrophobicity of the linker will depend on the assay conditions. However, the preferred length and/or composition of the linker can be determined using routine experimentation and the disclosure provided herein. Moreover, there is no requirement that the linker be optimized. Rather, it is only required that the linker operably link the probe to the cell.

As noted above, various types of cross linkers can be used to link the probe to the cell. Some non-limiting examples of cross linkers that may be used are described in Pierce Catalog and Handbook, 1994, Section O, under the heading: "Cross-linking/Protein Modification").

Determining Cells, Targets & Correlation

Cells can be determined using any applicable instrumentation and/or methodology. As noted above, microscopy, slide scanners and flow cytometers are particularly useful for determining stained cells. Other methods for determining stained cells can be found in WIPO application No. WO03/073817. In general, how the (stained) cells are determined is not a limitation of this method.

In some embodiments, the targets, as well as the cells, will comprise a detectable moiety or moieties (See for example; FIGS. 5 and 6). The methods selected to determine the cell will generally also be selected to determine the detectable moiety or moieties linked to the target.

As discussed in more detail below, the stained cells are correlated with the presence, absence, location and/or quantity of the target. This correlation can be made for both solution-based (FIGS. 5 and 6) and support-based assays (FIG. 4). In general, this correlation is possible by confirming that a cell-linker-probe/target complex formed, thereby enabling the correlation between the stained cell and the target associated with a condition of interest.

5. Various Embodiments of the Invention

It should be understood that the order of steps or order for performing certain actions is immaterial so long as the present teachings remain operable or unless otherwise specified. Moreover, in some embodiments, two or more steps or actions can be conducted simultaneously so long as the present teachings remain operable or unless otherwise specified.

Compositions:

In some embodiments, this invention pertains to a composition comprising a cell, a linker and a probe. The cell comprises a surface and a plurality of the same or different markers. The linker operably links the probe to the surface of the cell such that said probe is capable of binding to a target present outside of said cell. An illustration of a representative composition is found in FIG. 1. Said composition is referred to herein as a "Cell-Linker-Probe Complex".

The cell can, for example, be a bacteria or yeast. The cell can be a single cell of the tissue of a multicellular organism such as an animal, plant or human.

The probe can, for example, be a nucleic acid oligomer, a nucleic acid analog oligomer, a nucleic acid mimic oligomer or a chimera. The probe can, for example, be an antigen or an antibody.

In some embodiments, the markers can be labeled hybridization ligands that bind to rRNA of the cell. Said labeled hybridization ligands can be nucleic acid oligomers, nucleic acid analog oligomers, nucleic acid mimic oligomers or chimeras which are labeled with one or more detectable moieties. For example, said labeled hybridization ligands can be labeled with one or more fluorphores, chromophores, enzymes, haptens, radioisotopes, quantum dots or RFID tags, or any combination of two or more of the foregoing (i.e. as the detectable moieties). In some embodiments, the markers can be labeled antibodies (or antibody fragments) that bind to the cell surface and/or to components of the cell.

Regardless of the nature of the marker, said cells become "stained" and therefore detectable using select instruments and/or associated protocols. For example, the "stained" cells can be determined using a fluorescent microscope, slide scanner or flow cytometer. Said instruments can be used to identify, locate and/or quantify said stained cells of a Cell-Linker-Probe Complex, and by implication identify, locate and/or quantify the linked probe and its related target if the probe is bound thereto.

According to practice of embodiments of the presently described invention, the probe selectively binds to its respective target under suitable hybridization (binding) conditions. Thus, in some embodiments, this invention is further directed to a composition (i.e. a complex) comprising a cell, a linker, a probe and a target. The cell comprises a surface and a plurality of the same or different markers. The linker operably links the probe to the surface of the cell such that said probe binds to the target existing outside of said cell. An illustration of a representative composition is found in FIG. 2. Said composition is referred to herein as a "Cell-Linker-Probe/ Target Complex". As noted above, instruments/protocols can be used to identify, locate and/or quantify said stained cells of a Cell-Linker-Probe/Target Complex, and by implication the identity, locate and/or quantify of the linked target.

Methods:

In some embodiments, this invention pertains to a method comprising:

a) contacting a sample comprising a target with a composition comprising a cell, a linker and a probe; wherein; i) said cell comprises a surface and a plurality of same or different markers, wherein said markers, in the aggregate, render said cell determinable (i.e. the markers stain the cell); and ii) said linker operably links said probe to said surface of said cell to thereby form a cell-linker-probe complex, such that said probe is capable of binding to said target present outside of said cell; and wherein said contacting occurs under conditions suitable (i.e. suitable hybridization conditions or suitable binding conditions, as appropriate) for said probe to (selectively) bind to said target; and b) forming a cell-linker-probe/target complex;

c) determining presence, location and/or quantity of said markers associated with said cell; and d) correlating the presence, location and/or quantity of said markers of said cell with a presence, location and/or quantity of said target.

It is to be understood that when referring to "bind" or "binding" with respect to the above described method, if the probe is a hybridization probe, the terms "bind" and/or "binding" is/are intended to mean "hybridize" or "hybridizing" in this context.

An example of forming the cell-linker-probe/target complex from the target and a cell-linker-probe complex is illustrated in FIG. 3, wherein the target is support-bound (i.e. linked to a surface by a linker). Consequently, for this embodiment, the presence and/or location of the markers associated with the cell (wherein the cell-linker-probe complex is selectively bound to the surface) correlates with the presence and/or location of the target on the support.

In some embodiments, the sample can be an array wherein the array comprises a plurality of immobilized targets. FIG. 4 provides an illustration of an array comprising a plurality of different targets.

The sample can be a fluid. The sample can be a tissue.

The cell can, for example, be a bacteria or yeast. The cell can be a single cell of the tissue of a multicellular organism such as an animal, plant or human.

The probe can, for example, be a nucleic acid oligomer, a nucleic acid analog oligomer, a nucleic acid mimic oligomer or a chimera. The probe can, for example, be an antigen or an antibody.

In some embodiments, the markers can be labeled hybridization ligands that bind to rRNA of the cell. Said labeled hybridization ligands can be nucleic acid oligomers, nucleic acid analog oligomers, nucleic acid mimic oligomers or a chimeras which are labeled with one or more detectable moieties. For example, said labeled hybridization ligands can be labeled with one or more fluorphores, chromophores, enzymes, haptens, radioisotopes, quantum dots or RFID tags, or any combination of two or more of the foregoing (i.e. as the detectable moieties).

Accordingly, said cells become "stained" and therefore detectable using select instruments/protocols. For example, the "stained" cells are detectable using a fluorescent microscope, slide scanner or flow cytometer. Said instruments can be used to identify, locate and/or quantify said stained cells.

According to the methods, the cell-linker-probe/target complex is formed under conditions that promote selective binding of the probe to the target such that non-specific binding of the probe to non-targets is minimized or eliminated. For a more detailed discussion of specificity see the section entitled: "Specificity", above.

As noted above, various types of instruments can be used to determine the stained cells. Since the stained cells are stained with markers, the operating parameters of the instrument(s) are selected to determine the markers present in the cell(s). In this way, the presence of the markers correlates directly with the presence of the cell(s).

In some embodiments, merely a presence/absence determination is desired. For those applications, a flow cytometer would suffice since it is capable of determining the markers in the cells as each cell flows through the detector. For more information on flow cytometers and related protocols for cell analysis please see U.S. Pat. Nos. 5,981,180, 6,268,222 and 7,267,798.

For embodiments where knowledge of the location of the cell (for example on a surface) is desired, a microscope or slide scanner can be selected because each of these instruments is capable of determining location of the markers in at least 2 (if not 3) dimensions. Accordingly, a microscope or slide scanner can be used for determining location of the markers (and by inference location of the stained cells) on a surface or an array. In some cases, the cells themselves can be observed, including the morphology of the cell(s), which morphology may be useful to confirm identity (as discussed above).

According to the method, the final step involves correlating the presence and/or location of the markers of the cell with presence and/or location of the target. For embodiments where the target is support-bound, this becomes a fairly straightforward task. Specifically, the cell-target-probe complex specifically interacts with, and becomes specifically immobilized to, the surface where the corresponding target to the probe of the cell-linker-probe complex exists (i.e. the cell-linker-probe/target complex forms where the target is immobilized to the surface). Accordingly, the presence and/or location of the stained cell(s) of the cell-linker-probe complex on the surface (or at a location on the surface) directly correlates with the presence and/or location of the target. By implication, the absence of a signal on the surface, or at locations where possible targets exist, will confirm the absence of the target sought to be determined on the surface or at that any particular location on the surface. In some embodiments, it may be possible to quantify the amount of target on the surface.

These principles likewise apply to tissue samples. In particular, the cell-probe-linker/target complex will form where (and if) the target is present in the tissue. Consequently, if the target is present, the presence and/or location of the cell of the cell-linker-probe complex in the tissue directly correlates with the presence and/or location of the target. By implication, the absence of a signal on the surface, or at locations where possible targets exist, will confirm the absence of the target sought to be determined in the tissue. In this way the presence and/or location of the markers of the stained cell(s) correlate with presence and/or location of the target in the tissue. In some embodiments, it may be possible to quantify the amount of target in the tissue.

It is to be understood that in some embodiments, washing of the sample (e.g. an array or tissue) may be used to remove non-specifically bound cell-linker-probe complex(es) and thereby improve upon the reliability of the method. Persons of skill in the art will know how and when to perform such washing steps and be able to select effective reagents and procedures.

In some embodiments (e.g. where the sample is a fluid), the target itself can be labeled with one or more detectable moieties. Where the target itself is labeled, it is preferentially (but not necessarily) labeled with a moiety or moieties that are independently detectable as compared with the detectable moiety or moieties associated with the markers used to mark the cells. In this way, detection of the moiety or moieties that mark the cell in combination with detection of moiety or moieties that mark the target associated with a single composition (i.e. cell-linker-probe/target complex) will confirm the presence and/or location of the cell-linker-probe/target complex. In this way the presence and/or location of the markers of the cell correlate with presence and/or location of the target.

An example of this embodiment is illustrated in FIG. 5. According to this illustration, the cell-linker-probe/target composition will comprise the purple detectable moiety (label) and the green detectable moiety (label). In this way the presence and/or location of the markers of the cell correlate with presence and/or location of the target. Because the cell-linker-probe complexes bearing blue, red or cyan markers don't comprise the probes for the select target, the purple label (and hence the target) does not associate/correlate with those compositions. Thus, the cell-linker-probe/target complex (comprising both a purple and green label) can be distinguished from the other cell-linker-probe complexes, for example, by flow cytometer having a detector set to screen for the purple label in combination with the other colored labels (i.e. the blue, red, green or cyan labels; see FIG. 5) with respect to a single composition.

Multiplex Method(s):

In some embodiments, this invention pertains to a multiplex method comprising:

a) contacting a sample with at least two different compositions; each of said at least two different compositions comprising: a cell (that differs from the other cell or cells of the other of said at least two different compositions), a linker and a probe, wherein: 1) said cell comprises a surface and a plurality of the same or different markers, wherein said markers, in the aggregate, render said cell uniquely determinable as compared with said other cell or cells of said other of said at least two different compositions; and 2) said linker operably links said probe to said surface of said cell, to thereby form a cell-linker-probe complex, such that said probe is capable of binding to a select target and wherein the contacting occurs under conditions suitable (i.e. suitable hybridization conditions or suitable binding conditions as the case may be) for the probe to (selectively) bind to said select target, if present, in the sample. The method further comprises: b) forming a cell-linker-probe/select target complex from at least one of said at least two different compositions; provided that the select target is present in said sample and further provided that said probe of each of said at least two different compositions selectively binds to a different select target; c) determining presence, location and/or quantity of each uniquely determinable cell associated with each different composition of said at least two different compositions; and d) correlating the presence, location and/or quantity of each uniquely determinable cell with a presence, location and/or quantity of each different select target, if present, in the sample.

According to the methods, each cell-linker-probe/target complex is formed under conditions that promote selective binding of each respective probe to its respective select target such that non-specific binding of the probe to non-targets is minimized or eliminated. For a more detailed discussion of specificity see the section entitled: "Specificity", above.

It is to be understood that when referring to "bind" or "binding" with respect to the above described method, if the probe is a hybridization probe, the terms "bind" and/or "binding" is/are intended to mean "hybridize" or "hybridizing" in this context.

In some embodiments, the sample can be an array wherein the array comprises a plurality of immobilized targets. For example, FIG. 4c illustrates an example of said multiple method whereby a mixture of four different uniquely identifiable (red, blue, green and cyan labeled) cell-linker-probe complexes is contacted with a 4×5 target array wherein each spot (e.g. distinct array location) on the array comprises a different covalently linked target molecule (i.e. 20 different targets). As can be seen in the illustration provided in FIG. 4c, each of the cell-linker-probe complexes binds to a different spot (i.e. array location) wherein binding correlates with the select target for each different probe of the different cell-linker-probe complexes. Thus, observing the red cell at array location B1 reveals that the target to the cell-linker-probe complex marked with the red stain is present at location B1. Similarly, observing each of the blue, green and cyan cells at array locations A5, C3 and D2, respectively, reveals that the select target for each of the corresponding marked cell-linker-probe complexes is present at these respective array locations.

It is to be understood however that the sample need not be an array. The sample can be a fluid. The sample can be a tissue.

The cell can, for example, be a bacteria or yeast. The cell can be a single cell of the tissue of a multicellular organism such as an animal, plant or human.

The probe can, for example, be a nucleic acid oligomer, a nucleic acid analog oligomer, a nucleic acid mimic oligomer or a chimera. The probe can, for example, be an antigen or an antibody.

In some embodiments, the markers can be labeled hybridization ligands that bind to rRNA of the cell. Said labeled hybridization ligands can be nucleic acid oligomers, nucleic acid analog oligomers, nucleic acid mimic oligomers or a chimeras which are labeled with one or more detectable moieties. For example, said labeled hybridization ligands can be labeled with one or more fluorophores, chromophores, enzymes, haptens, radioisotopes, quantum dots or RFID tags, or any combination of two or more of the foregoing (i.e. as the detectable moieties).

As previously noted, said cells become "stained" and therefore detectable using select instruments/protocols. For multiplex methods, the cells are uniquely identifiable. Thus, different cells comprise different markers, different combinations of markers or different ratios of the combination of the same markers such that the different cells are uniquely identifiable. As discussed previously, "stained" cells may be detectable using a fluorescent microscope, slide scanner or flow cytometer (depending on the nature of the marker(s)). Said instruments can be used to identify, locate and/or quantify said stained cells.

Further reference is made to the section above entitled "Methods" for a discussion of various ways to correlate markers of the respective cells with respective targets in array, tissue and fluid samples. It is to be understood that said correlations are equally applicable to the multiplex methods provided that the independently detectable cells are used to make independent determinations with respect to each of the respective select targets.

An example of a solution-based multiplex method is illustrated in FIG. 6. According to this illustration, each cell-linker-probe/target complex will comprise the purple detectable moiety (label) linked to each respective target and a detectable moiety (label) based on the cell to which the corresponding probe is linked. In this way the presence and/or location of the markers of the respective cell correlates with presence and/or location of the respective target. Because the sample does not comprise the select target for the cell-linker-probe complex bearing blue markers, the purple label (and hence the target) does not associate/correlate with the cell-linker-probe complex marked with the blue markers. Thus, the cell-linker-probe/target complexes (comprising both a purple and respective, red, green or cyan labels) can be distinguished, for example, by flow cytometry.

Quantification

In some embodiments, the methods described above can include a quantification step whereby the target is quantified (rather than or in addition to determining the presence, absence and/or location of the target). Whether or not quantification is possible will depend on the nature of the detectable moiety or moieties selected and the instrumentation and/or methodology selected for detecting the detectable moiety or moieties. Persons of skill in the art will be able to select suitable labels, instruments and methods for quantification using no more than routine experimentation in combination with the guidance provided herein. Quantification can be applied to methods for determining single targets as well as to multiplex methods.

REFERENCES

US Patents & Patent Application Publications

1. U.S. Pat. No. 5,225,326 to Bresser et al.
2. U.S. Pat. No. 5,747,349 to Van Den Engh et al.
3. U.S. Pat. No. 5,981,180 to Chandler et al.
4. U.S. Pat. No. 6,110,676 to Coull et al.
5. U.S. Pat. No. 6,197,513 to Coull et al.
5. U.S. Pat. No. 6,268,222 to Chandler et al.
6. U.S. Pat. No. 6,664,045 to Hyldig-Nielsen et al.
7. U.S. Pat. No. 6,449,562 to Chandler et al.
8. U.S. Pat. No. 7,197,286 to Morris et al.
9. U.S. Pat. No. 7,267,798 to Chandler et al.
10. U.S. Pat. No. 7,494,776 to Wallace et al.
11. US 2001/0055764 to Empedocles et al.
12. US 2002/0142326 to Coull et al.
13. US 2005/0009052 to Supek et al.
14. US 2005/0277197 to Chandler et al.
15. US 2006/0199196 to O'Banion et al.

Foreign Patent Publications

1. WO 01/12862 to Stuelpnagel et al.
2. WO 01/00876 to Mirkin et al.
3. WO 03/07817 to Straus, D.

Product Literature/Scientific Publications

1. Product Literature & Product Listing, eBioscience, eFluor Nanocrystals, Website_ebioscience.com, October 2009, 10 pages.
2. Product Literature, Invitrogen, *Tools for microbiology detection and research*, 2007, 20 pages.
3. Product Literature, Invitrogen, *Alexa Fluor Dye Selection Guide*, available as of October, 2009, 48 pages.
4. Product Literature, Invitrogen, *Chemical Crosslinkinq Reagents*, Section 5.2 of Molecular Probes The Handbook, available as of October, 2009, 14 pages.
5. Product Literature, Invitrogen, *Antibody Labeling From A to Z*, available as of October, 2009, 12 pages.
6. Product Literature, Carestream Health, *Kodak X-Sight Nanosphere Secondary Antibody Conjugates & Dye Conjugates*, available as of October 2009, 5 pages.
7. Bearinger et al., *Chemical Tethering Of Motile Bacteria To Silicon Surfaces*, BioTechniques, 46(3): 209-216 (2009).
8. Miller, Steve, *Luciferase+Quantum Dot=Self Illuminating Nanocrystal Technologies*, Zymera, Inc. & Zymera 2009 Product List, 3 pages.
9. Jarvis et al., *Practical Platform*, CENEAR, 87(30): 34-36 (2009).
10. Jin et al., *A Generalized Kinetic Model For Amine Modification Of Proteins With Application To Phage Display*, BioTechniques, 46(3): 175-182 (2009).

While the present teachings are described in conjunction with various embodiments, it is not intended that the present teachings be limited to such embodiments. On the contrary, the present teachings encompass various alternatives, modifications and equivalents, as will be appreciated by those of skill in the art.

I claim:

1. A composition comprising an internally stained cell, a linker and a probe; wherein,
   a) said internally stained cell comprises a surface and a plurality of the same or different markers within said cell that internally stain said cell; and
   b) said linker operably links said probe to said surface of said internally stained cell such that said probe is capable of binding to a target present outside of said cell;
   wherein said probe is a nucleic acid oligomer, a nucleic acid analog oligomer, a nucleic acid mimic oligomer or chimera.

2. The composition of claim 1, wherein said cell is a bacteria or yeast.

3. The composition of claim 1, wherein said markers are labeled hybridization ligands that bind to rRNA of said cell.

4. The composition of claim 3, wherein said labeled hybridization ligands are labeled with one or more fluorophores, chromophores, spin labels, enzymes, haptens, radio-isotopes, chemiluminescent compounds, quantum dots or RFID tags; or any combination of two or more of the foregoing.

5. The composition of claim 1, wherein said probe is a nucleic acid analog oligomer.

6. The composition of claim 1, wherein said probe is a nucleic acid mimic oligomer.

7. The composition of claim 1, wherein said probe is a chimera.

8. The composition of claim 1, wherein said probe is a peptide nucleic acid.

9. The composition of claim 1, wherein said composition is immobilized to a spot on an array.

10. The composition of claim 1, wherein said linker has the formula: —Y—(O, —(CW$_2$)$_n$)$_o$—Z—, wherein:
    the group Y is a single bond, —(CW$_2$)$_p$—, —C(O)(CW$_2$)$_p$—, —C(S)(CW$_2$)$_p$— or —S(O$_2$)(CW$_2$)$_p$;
    the group Z is Y, NH, NR$^2$, S or O;
    each W is independently H, R$^2$, —OR$^2$, F, Cl, Br or I;
    wherein, each R$^2$ is independently selected from the group consisting of: —CX$_3$, —CX$_2$CX$_3$, —CX$_2$CX$_2$CX$_3$, —CX$_2$CX(CX$_3$)$_2$, and —C(CX$_3$)$_3$ and each X is independently H, F, Cl, Br or I;
    each m is independently 0 or 1; and
    each n, o and p is independently an integer from 0 to 10.

* * * * *